US012698464B2

(12) United States Patent
Locascio

(10) Patent No.: US 12,698,464 B2
(45) Date of Patent: Aug. 4, 2026

(54) INTEGRATED METHANOL SYNTHESIS AND FERMENTATION SYSTEM

(71) Applicant: Arbela Laboratories, Inc., Randolph, NJ (US)

(72) Inventor: Michael Locascio, Randolph, NJ (US)

(73) Assignee: Arbela Laboratories, Inc., Randolph, NJ (US)

( * ) Notice: Subject to any disclaimer, the term of this patent is extended or adjusted under 35 U.S.C. 154(b) by 757 days.

(21) Appl. No.: 17/798,240

(22) PCT Filed: Feb. 10, 2021

(86) PCT No.: PCT/US2021/017495
§ 371 (c)(1),
(2) Date: Aug. 8, 2022

(87) PCT Pub. No.: WO2021/163217
PCT Pub. Date: Aug. 19, 2021

(65) Prior Publication Data

US 2023/0080511 A1 Mar. 16, 2023

Related U.S. Application Data

(60) Provisional application No. 62/995,721, filed on Feb. 11, 2020.

(51) Int. Cl.
*C12M 1/00* (2006.01)
*C12M 1/02* (2006.01)
*C12M 1/34* (2006.01)
*C12N 1/205* (2026.01)

(52) U.S. Cl.
CPC ............ *C12M 21/12* (2013.01); *C12M 27/00* (2013.01); *C12M 29/06* (2013.01); *C12M 41/12* (2013.01); *C12N 1/205* (2021.05)

(58) Field of Classification Search
CPC ...... C12M 21/12; C12M 29/06; C12M 41/12; C12N 1/205
See application file for complete search history.

(56) References Cited

U.S. PATENT DOCUMENTS

| | | | | |
|---|---|---|---|---|
| 4,048,017 A | 9/1977 | Roesler | | |
| 8,663,392 B2 * | 3/2014 | Zhang | D21C 3/22 127/9 | |
| 8,951,490 B2 * | 2/2015 | Okumura | B01D 53/04 423/220 | |
| 9,957,161 B2 * | 5/2018 | Merritt, Jr. | C10G 2/30 | |
| 2007/0004809 A1 | 1/2007 | Lattner et al. | | |
| 2011/0223650 A1 * | 9/2011 | Saunders | B01D 63/10 435/283.1 | |
| 2015/0140640 A1 * | 5/2015 | Reed | C12P 5/026 435/252.3 | |
| 2018/0245108 A1 * | 8/2018 | Reed | C12M 29/08 | |
| 2019/0144890 A1 * | 5/2019 | Subbian | B01F 23/231 435/296.1 | |

FOREIGN PATENT DOCUMENTS

| | | | |
|---|---|---|---|
| WO | 2002/086135 A2 | 10/2002 | |
| WO | 2010/014774 A2 | 2/2010 | |
| WO | WO-2017153396 A1 * | 9/2017 | C12P 23/00 |

OTHER PUBLICATIONS

Chistoserdova et al. "Methylotrophy in Methylobacterium extorquens AM1 from a genomic point of view." Journal of bacteriology 185.10 (2003): 2980-2987. (Year: 2003).*
Dimitriou et al. (2018. "Techno-economic and uncertainty analysis of Biomass to Liquid (BTL) systems for transport fuel production." Renewable and sustainable energy reviews, 88, 160-175) (Year: 2018).*
Zhang et al. 2018. "Current advance in bioconversion of methanol to chemicals." Biotechnol Biofuels 11, 260. https://doi.org/10.1186/s13068-018-1265-y. (Year: 2018).*
Li et al. 2012. "Evaluation of a biomass drying process using waste heat from process industries: A case study." Applied Thermal Engineering, 35, pp. 71-80 (Year: 2012).*
English Translation of the description of WO-2017153396; originally published Sep. 14, 2017; obtained from Espacenet Patent Translate tool (EPO) at <https://worldwide.espacenet.com/patent/search?q=pn%3DWO2017153396A1> (Year: 2017).*
International Search Report and Written Opinion of International Application No. PCT/US2021/017495 mailed May 3, 2021, 10 pgs.
Dimitriou et al., "Techno-economic and uncertainty analysis of Biomass to Liquid (BTL) systems for transport fuel production. Renewable and Sustainable Energy Reviews", May 2018, pp. 160-175, vol. 88, Elsevier Ltd.

* cited by examiner

*Primary Examiner* — Anand U Desai
*Assistant Examiner* — Andrew T Moehlman
(74) *Attorney, Agent, or Firm* — Lowenstein Sandler LLP

(57) ABSTRACT

The present disclosure relates to an integrated methanol synthesis and fermentation system for the production of whole cells and biomolecules, and methods of using the same. In one embodiment, a system comprises a methanol synthesis apparatus adapted to produce unrefined methanol; a mixing apparatus adapted to receive unrefined methanol from the methanol synthesis apparatus; and a metering apparatus having at least one first input port in communication with mixing apparatus and at least one second output port in communication with a fermentation vessel.

16 Claims, 3 Drawing Sheets

METHOD 300

START

Provide a growth medium comprising unrefined methanol

310

Meter the growth medium into a fermentation vessel comprising an aqueous fermentation medium

320

Introduce an oxygen-containing gas into the aqueous fermentation medium within the fermentation vessel

330

Separate, from the aqueous fermentation medium, whole cells or excreted biomolecules

340

END

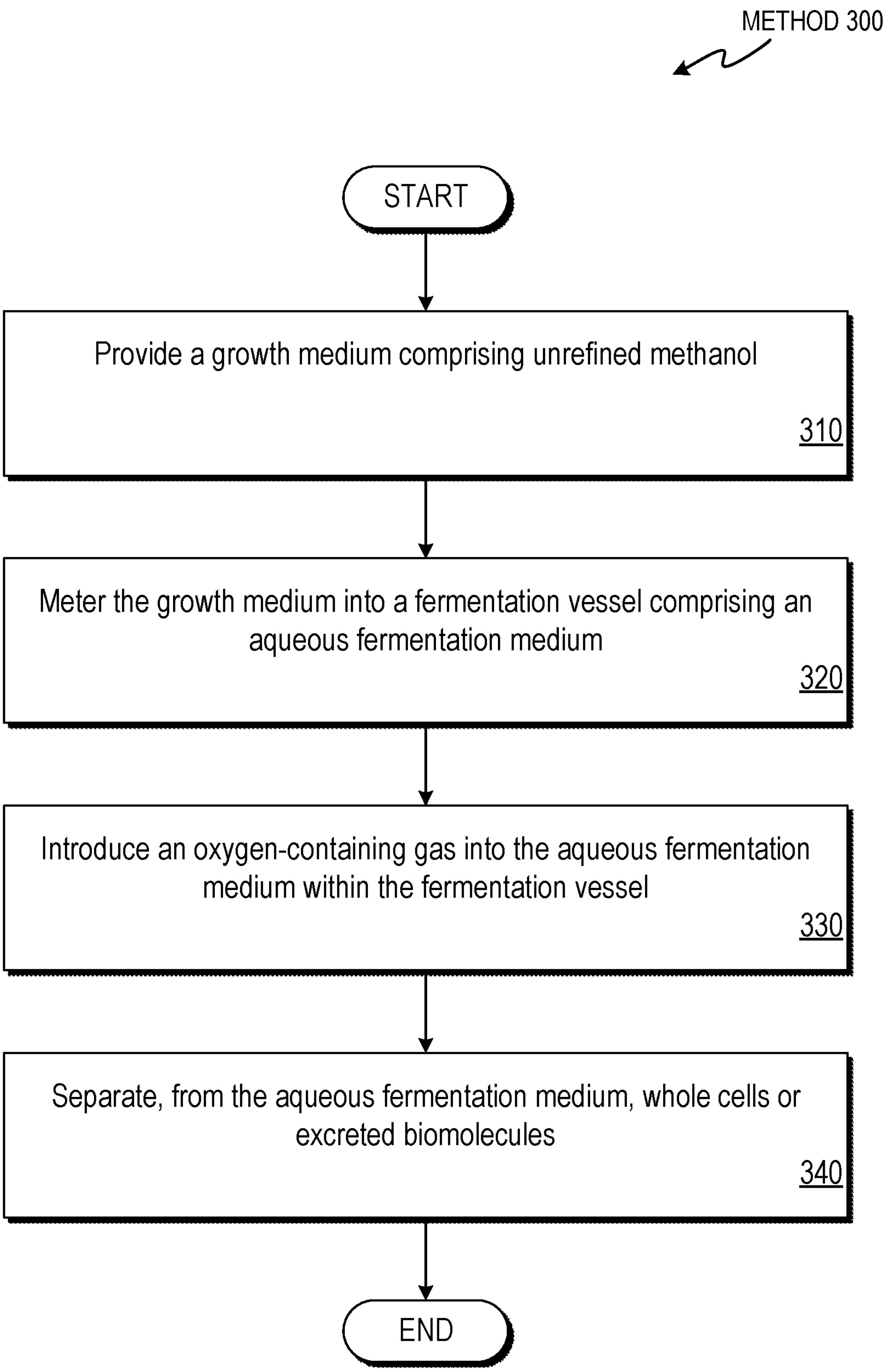

FIG. 3

INTEGRATED METHANOL SYNTHESIS AND FERMENTATION SYSTEM

CROSS-REFERENCE TO RELATED APPLICATION(S)

This application claims the benefit of priority of U.S. Provisional Patent Application No. 62/995,721, filed Feb. 11, 2020, the disclosure of which is hereby incorporated by reference herein in its entirety.

TECHNICAL FIELD

The present disclosure is directed to biomolecule production and, more specifically, to systems and methods of producing biomolecules, such as recombinant proteins, and single cell protein (whole cells) via fermentation processes.

BACKGROUND

Biomolecules are typically large complex molecules produced by living organisms that include, but are not limited to peptides, proteins, enzymes, fatty acids, carotenoids, flavonoids, carbohydrates, and biopolymers (e.g., polyhydoxyalkanoates including polyhydroxybutyrate, chitin, cellulose, and pullulan). Biomolecular synthesis via fermentation is a well-established process that utilizes numerous types of single cell organisms ranging from bacteria, yeasts, mammalian cells, and algae typically, but not exclusively, grown in closed vessels under strict temperature conditions, aerobic or anaerobic conditions, and other conditions. In addition to complex biomolecules, simpler molecules, including low molecular weight alcohols, acids, and ketones, are commonly produced via fermentation.

Technological advancements over the past several decades have allowed for genetic engineering of many organism types that direct them to produce selected molecules. Alternatively, unaltered cells also naturally produce a variety of biomolecules and are often grown as sources of bulk protein or enzymes. Biomolecules including, but not limited to, proteins and other molecules described above, can either be excreted into a fermentation medium in which the single cell organisms are growing or are alternatively retained within the cell. In the former situation, the biomolecule can be separate from the fermentation medium using techniques including, but not limited to, ultrafiltration, precipitation, and high-performance liquid chromatography (HPLC). In the latter situation, the desired biomolecules may either be retained within whole cells (which are typically dried) or separated via cell lysing/rupturing or other well-known separation and purification processes. Applications of proteins produced via fermentation processes include biologic pharmaceuticals, analytic proteins, industrial enzymes, and bulk protein for human and animal nutrition (referred to as "single cell protein," or "SCP"). Other fermentation applications include, but are not limited to, the production of nutritional supplements, biopolymers used in packaging and medical applications.

SUMMARY

The following summary presents a simplified summary of various aspects of the present disclosure in order to provide a basic understanding of such aspects. This summary is not an extensive overview of the disclosure. It is intended to neither identify key or critical elements of the disclosure, nor delineate any scope of the particular embodiments of the disclosure or any scope of the claims. Its purpose is to present some concepts of the disclosure in a simplified form as a prelude to the more detailed description that is presented later.

Aspects of the present disclosure relate to a system and method for producing biomolecules or whole cells. In one aspect, a method comprises: providing a growth medium comprising unrefined methanol; metering the growth medium into a fermentation vessel comprising an aqueous fermentation medium; introducing an oxygen-containing gas into the aqueous fermentation medium within the fermentation vessel for a duration sufficient to expand a population of methylotrophic organisms within the aqueous fermentation medium; and separating, from the aqueous fermentation medium, whole cells of the methylotrophic organisms or biomolecules excreted by the methylotrophic organisms into the aqueous fermentation medium.

In one embodiment, the unrefined methanol is derived from a methanol synthesis apparatus without being subjected to a distillation process, or by being subjected to a subset of steps of the distillation process. In one embodiment, the unrefined methanol comprises greater than about 0.5% water and/or less than about 0.1% alcohol having more than 1 carbon atom.

In one embodiment, the oxygen-containing gas is introduced into the aqueous fermentation medium via jet aeration, surface aeration, or fine bubble diffusers. In one embodiment, the oxygen-containing gas comprises air, a mixture of oxygen and at least one other gas, or purified oxygen. In one embodiment, the oxygen-containing gas is introduced into the aqueous fermentation medium in a form of bubbles having a median diameter of less than about 200 nm.

In one embodiment, the methylotrophic organisms comprise one or more of *Pichia pastoris, Methylophilus methylotrophus, Methylobacterium extorquens, Methylomonas methanolica*, or *Pseudomonas methanolica.*

In one embodiment, the methylotrophic organisms utilize a ribose monophosphate pathway, a serine pathway, an alcohol oxidase 1 pathway, and/or an alcohol oxidase 2 pathway.

In one embodiment the whole cells are separated from the aqueous fermentation medium by: extracting a portion of the aqueous fermentation medium comprising the whole cells; concentrating the whole cells into a first stream and whole cell-depleted fermentation medium into a second stream; and optionally reintroducing the second stream into the fermentation vessel. In one embodiment, the method further comprises passing the portion of the aqueous fermentation medium through a filter comprising pores. In one embodiment, the pores have an average diameter of less than average diameters of the whole cells. In one embodiment, concentrating the whole cells into the first stream comprises exposing the aqueous fermentation medium to centrifugal force.

In one embodiment, the method further comprises drying the concentrated whole cells via exposure to superheated steam. In one embodiment, the superheated steam is derived from a methanol synthesis apparatus. In one embodiment, the method further comprises reintroducing steam or superheated steam back into the methanol synthesis apparatus after drying the concentrated whole cells.

In one embodiment, the method further comprises: drying the concentrated whole cells via exposure to hot gas; or lysing the whole cells via exposure to the hot gas. In one embodiment, the hot gas generated from steam from a methanol synthesis apparatus.

In one embodiment, the method further comprises drying the concentrated whole cells via spray drying, microwave drying, freeze drying, or lyophilization.

In one embodiment, the method further comprises: extracting a carbon dioxide-containing waste gas mixture evolved from the whole cells in fermentation vessel; and separating carbon dioxide from other gases within the waste gas mixture into a concentrated carbon dioxide gas stream and a carbon dioxide-depleted gas stream. In one embodiment, the carbon dioxide is separated from the other gases via exposure to molecules comprising one or more amine moieties or exposure to size selective molecular sieves or zeolites. In one embodiment, the method further comprises introducing the concentrated carbon dioxide gas stream into a methanol synthesis apparatus. In one embodiment, the method further comprises introducing the carbon dioxide-depleted gas stream into the fermentation vessel.

In one embodiment, the method further comprises maintaining a temperature of aqueous fermentation medium at below 120° F. using a chilling apparatus. In one embodiment, the chilling apparatus comprises an adsorption chiller. In one embodiment, thermal energy used by adsorption chiller is derived from steam generated by a methanol synthesis apparatus.

In another aspect, a system for producing biomolecules comprises: a methanol synthesis apparatus adapted to produce unrefined methanol; a mixing apparatus adapted to receive unrefined methanol from the methanol synthesis apparatus; and a metering apparatus having at least one first input port in communication with mixing apparatus and at least one second output port in communication with a fermentation vessel.

In one embodiment, the mixing apparatus is further adapted to add a nitrogen source, nutrients for cell growth, and water.

In one embodiment, the methanol synthesis apparatus is in direct communication with the mixing apparatus.

In one embodiment, the fermentation vessel comprises at least one outlet port to extract a carbon dioxide-containing gas, at least one output port to extract liquid contents of fermentation vessel including an aqueous fermentation medium and/or a whole cell-containing aqueous fermentation medium, and a port to receive an oxygen-containing gas. In one embodiment, the fermentation vessel is in communication with a temperature control apparatus to maintain a temperature of liquid contents of fermentation vessel at below 120° F. In one embodiment, the temperature control apparatus comprises a chiller. In one embodiment, the chiller is an absorption chiller adapted to receive a high temperature steam input and produce a low temperature steam output or water output. In one embodiment, the high temperature steam input is derived from the methanol synthesis apparatus. In one embodiment, the absorption chiller is adapted to reintroduce the low temperature steam output or water output into the methanol synthesis apparatus.

In one embodiment, the methanol synthesis apparatus comprises a syngas production apparatus in communication with an optional water gas shift reactor in communication with syngas to methanol reactor. In one embodiment, the syngas production apparatus is adapted to derive syngas from steam methane reforming, partial oxidation of natural gas, water gas shift reaction of hydrogen and carbon dioxide, gasification of coal, gasification of biomass, gasification of sewage sludge or gasification of paper, wood, tires, or municipal waste.

In one embodiment, the system further comprises an oxygen introduction apparatus having at least one input port in communication with an oxygen containing gas and at least one output port in communication with the fermentation vessel. In one embodiment, the oxygen introduction apparatus comprises a jet aerator, surface aerators, or fine bubble diffusers. In one embodiment, the oxygen introduction apparatus is adapted to generate bubbles of oxygen-containing gas within an aqueous medium having a median diameter of less than about 200 nm.

In one embodiment, the system further comprises a gas purification apparatus comprising: at least one input port in communication an outlet port of the fermentation vessel to receive a carbon dioxide-containing gas stream from the fermentation vessel; at least one primary output port that provides the carbon dioxide-containing gas stream to the methanol synthesis apparatus; and optionally at least one secondary output port that diverts a carbon dioxide-depleted gas stream. In one embodiment, the at least one secondary output port of the gas purification apparatus is adapted to provide the carbon dioxide-depleted gas stream to at least one input port of an oxygen introduction apparatus in communication with the fermentation vessel. In one embodiment, the gas purification apparatus comprises molecules having one or more amine moieties in a liquid, solid, or polymer form adapted for use in an adsorbent in a pressure swing absorption or temperature swing absorption system. In one embodiment, the gas purification apparatus comprises: size selective molecular sieves or zeolites adapted for use in an adsorbent in a pressure swing absorption or temperature swing absorption system; or a membrane-based separation apparatus.

In another aspect, a separation apparatus comprises: at least one input port in communication with a fermentation vessel and adapted to receive whole cells of an aqueous fermentation medium of the fermentation vessel; at least one primary output port adapted to provide whole cell-rich stream; and at least one secondary output port adapted to provide a whole cell-depleted stream to the fermentation vessel via an input port on the fermentation vessel.

In one embodiment, the at least one primary output port is in communication with a drying apparatus for drying or lysing whole cells. In one embodiment, the drying apparatus comprises a superheated steam dryer adapted to provide superheated steam derived from a methanol synthesis apparatus. In one embodiment, the drying apparatus comprises a lyophilizer, a freeze dryer, a hot air dryer, or a steam dryer. In one embodiment, the separation apparatus further comprises a membrane or filter comprising a plurality of pores. In one embodiment, the pores have an average diameter of less than mean diameters of whole cells for which the separation apparatus is adapted to separate.

In another aspect, any embodiments of the foregoing systems may be adapted to perform any embodiments of the foregoing methods.

In another aspect, any embodiments of the foregoing systems may comprise any embodiments of the foregoing separation apparatuses.

As used herein, the singular forms “a,” “an,” and “the” include plural references unless the context clearly indicates otherwise. Thus, for example, reference to “a protein” can include a single protein, multiple proteins of a single type, and mixtures of two or more different proteins.

Also as used herein, the term “about” in connection with a measured quantity, refers to the normal variations in that measured quantity, as expected by one of ordinary skill in the art in making the measurement and exercising a level of care commensurate with the objective of measurement and the precision of the measuring equipment. In certain embodiments, the term "about" includes the recited number±1%, such that "about 10" would include 9.9 to 10.1 and all values in between.

Also as used herein, "protein" has its ordinary and customary meaning in the art and includes, and refers to a polypeptide (i.e., a string of at least two amino acids linked to one another by peptide bonds). Polypeptides may include natural amino acids, non-natural amino acids, synthetic amino acids, amino acid analogs, and combinations thereof. The term "peptide" is typically used to refer to a polypeptide having a length of less than about 50 amino acids. Proteins may include moieties other than amino acids (e.g., glycoproteins) and may be processed or modified. A protein can be a complete polypeptide chain as produced by a cell, or can be a functional portion thereof. A protein can include more than one polypeptide chain which may be chemically linked (e.g., by a disulfide bond), non-chemically linked (e.g., by hydrogen bonding), or both. Polypeptides may contain L-amino acids, D-amino acids, or both, and may contain any of a variety of amino acid modifications or analogs known in the art.

BRIEF DESCRIPTION OF THE DRAWINGS

The present disclosure is illustrated by way of example, and not by way of limitation, in the figures of the accompanying drawings, in which:

FIG. 3 is a flow diagram illustrating a method of producing biomolecules or whole cells in accordance with at least one embodiment of the disclosure.

DETAILED DESCRIPTION

Figure 1:
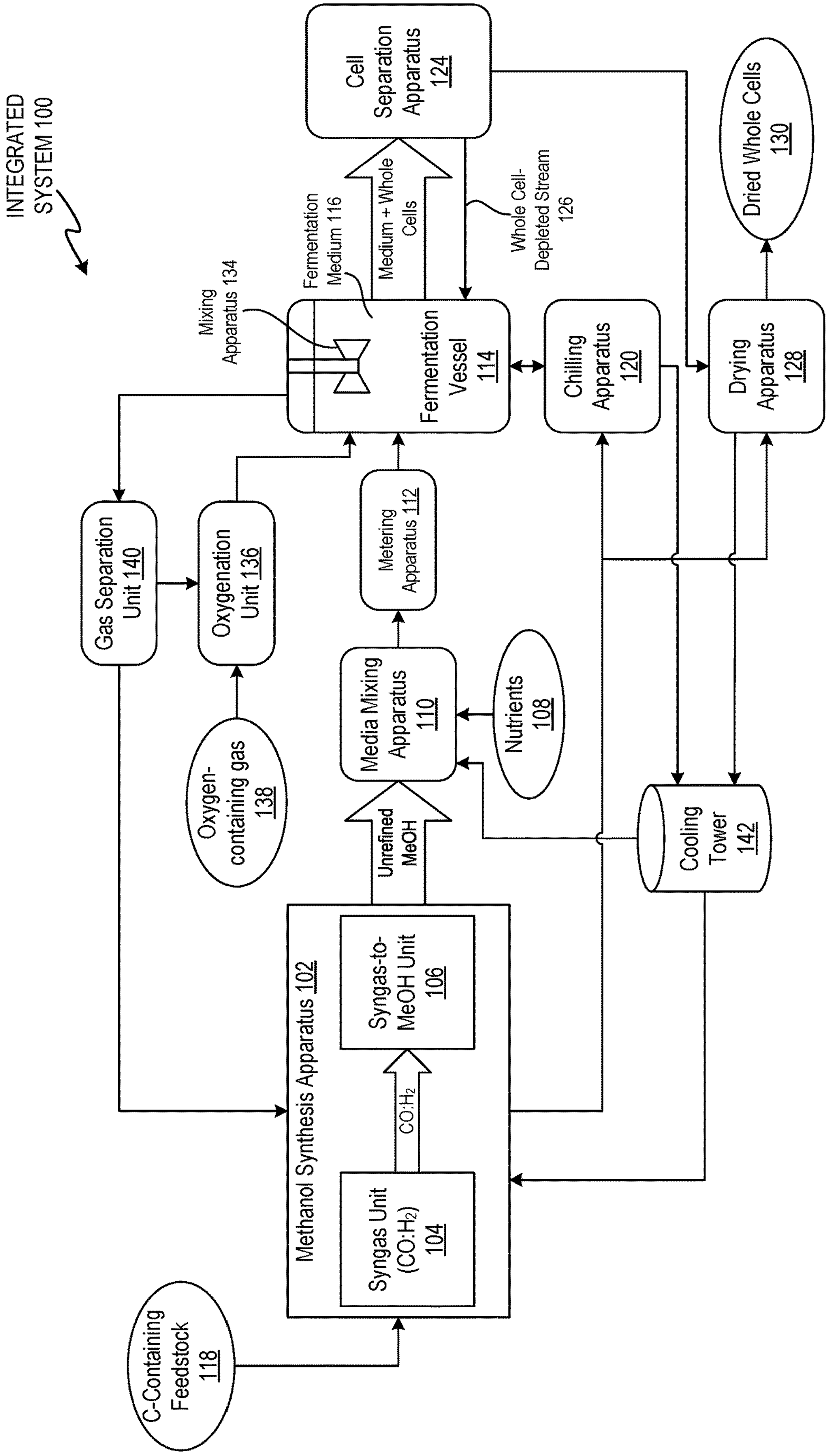
FIG. 1 is a block diagram illustrating an exemplary integrated system for growing and isolating whole cells in accordance with at least one embodiment of the disclosure.

The present disclosure is directed to a system and method to produce protein, oils, carotenoids, biopolymers, and other biomolecules is described herein. Specifically, embodiments relate to a system and method that integrates upstream methanol synthesis apparatus with midstream methylotroph fermentation and downstream separation and purification processes to greatly reduce overall cost of biomolecular production by eliminating the need for methanol distillation columns that are both costly and energy consuming. In some embodiments, the upstream methanol synthesis apparatus produces unrefined (crude) methanol comprising methanol and some smaller amount of water, higher alcohols, and other organic molecules. An exemplary composition of unrefined methanol is summarized in Table 1 below. As used herein, "unrefined methanol" refers to methanol compositions that have been produced without being subjected to any distillation or purification processes, or that have been produced using only a subset of steps that are generally used in distillation or purification processes. The unrefined methanol can be directly mixed with water and other nutrients and subsequently introduced into a fermentation vessel in which methylotroph organisms grow. Furthermore, a waste steam produced by the upstream methanol synthesis apparatus may be optionally used to dry extracted and purified whole cells or excreted biomolecules, and/or used to power absorption chillers to control the temperature of the fermentation vessel and/or used to power temperature swing adsorption units to create an oxygen rich stream from air or other oxygen containing gas. Moreover, carbon dioxide evolved by the respiration of the methylotrophs growing within the fermentation vessel can be extracted, purified (potentially using waste steam to power temperature swing adsorption units to separate carbon dioxide from fermentation offgas), and injected into the upstream methanol synthesis apparatus to increase methanol production output according to processes that would be appreciated by those of ordinary skill in the art.

TABLE 1

Exemplary composition of unrefined methanol

| Component | Concentration |
|---|---|
| Methanol | about 80% |
| $H_2O$ | about 20% |
| Ethanol | 300 ppm |
| Propanol | 200 ppm |
| Butanol | 80 ppm |
| Methyl Formate | 400 ppm |
| Dimethyl Ether | 100 ppm |
| Acetone | 10 ppm |
| Mixed alkanes (C2-C10) | 75 ppm |

Sugar, sugar derivatives, or glycerol are often used as carbon and energy sources for growing cells (with additional nitrogen, salts, and other nutrient additives). Some organisms can utilize other molecules as carbon and energy courses. For example, methylotrophs are microorganisms that can utilize methanol or other simple alcohols as carbon and energy sources.

Single cell protein (SCP) is an established technology already used for animal and human consumption albeit at far smaller scale than traditional sources of protein. SCP fermented on a methanol substrate using high protein content (60-80%) methylotrophic microorganisms offers a potential solution to produce protein needed for a growing population while greatly reducing the agricultural footprint. Protein can also be provided through the cultivation of various microbes and algae, preferably those which contain more than 30% protein in their biomass and which can provide a healthy balance of essential amino acids. In addition to direct use as SCP, microbes contribute to protein demand when they are used to upgrade the protein content or quality of fermented foods. Although, microbial protein provides a relatively small proportion of current human nutrition, the growing global demand for protein is likely to make SCP increasingly important. High growth rates or the ability to utilize unique substrates, such as $CO_2$, methane, or methanol, result in processes which offer much higher efficiency and/or sustainability than is possible from traditional agriculture.

SCP is currently produced from a limited number of microbial species, although the range of sources for SCP used in animal feed is broader than that approved for human consumption and is expanding. Products derived from algae, fungi (including yeast) and bacteria are all in use or under development. The production steps generally include (a) preparation of nutrient media, (b) cultivation, including solid state fermentation, (c) separation and concentration of SCP, and in some cases drying, and (d) final processing of SCP into ingredients and products. SCP for human consumption is generally produced from food grade substrates and regulatory issues must always be considered.

A wide range of fungi have been considered for use as SCP. Products from *Saccharomyces, Fusarium*, and *Torulopsis* are commercially available. Fungi grown as SCP will generally contain 30-50% protein. Methylotrophic yeasts, for example *Komagataella pastoris* (previously *Pichia pastoris*), produce biomass and protein from methanol. Bacteria also have a long history of use as SCP, particularly in animal feed. Bacterial SCP generally contains 50-80% protein on a dry weight basis. As with fungi, bacterial SCP has high nucleic acid content (8-12%), in particular RNA, and thus requires processing prior to usage as food/feed. In addition to protein, bacterial SCP provides some lipid and B group vitamins.

Methanol is generally synthesized from natural gas largely through multistage catalytic steam reformation, although coal, biomass, and other sources are also possible synthetic gas ("syngas") feedstocks for conversion to methanol. Furthermore, it is possible to react carbon dioxide with hydrogen derived from electrolysis of water to produce methanol. The general process includes: (1) natural gas desulfation and cleanup to create a purified methane stream; (2) methane reforming to produce $CO+H_2$ syngas; (3) catalytic methanol synthesis; and (4) distillation and purification to remove water and other contaminants. It is noted that the latter stage is energy intensive and requires substantial capital equipment. However, purified methanol is not required when used as a microbial fermentation feedstock as, in the present application, it is diluted in water to typically between 1% and 5% concentration. It is further noted that methane reforming does not typically produce an ideal ratio of hydrogen and carbon monoxide, as such intermediate reactions, such as water gas shift (WGS), may be used to adjust the stoichiometry. In addition, it known that the addition of $CO_2$ to the syngas and/or methanol synthesis step may facilitate stoichiometric adjustment and increase overall methanol output.

There are seven reforming processes available to produce syngas from natural gas/methane. The most common process is steam methane reforming (SMR), but alternative processes include partial oxidation (POx), dry-reforming, tri-reforming and several other known methods. In addition, alternative feedstocks other than natural gas may be used to produce syngas are known, including but not limited to coal, biomass, sewage sludge, etc. Furthermore, it is possible to create hydrogen through the electrolysis of water and, in combination with $CO_2$, be used to create syngas.

SMR, the most common method of producing syngas, involves the endothermic conversion of methane and water vapor at temperatures between 700° C. and 850° C. and pressures between 3-5 bar over an iron-based catalyst into syngas, where the input heat is often supplied via the combustion of some of the methane feed gas. The reaction is as follows:

$$CH_4 + H_2O + \text{heat} \longrightarrow CO + 3H_2 \ (\Delta H_r = 226 \text{ kJ/mol}).$$

Methanol can be manufactured from synthesis gas that is converted in a fixed bed reactor over a copper and zinc oxide coated alumina catalyst at 40-100 atm. The reaction is as follows:

$$CO + 2H_2 \longrightarrow CH_3OH \ (H_r = -91 \text{ kJ/mol}).$$

All fermentation applications are very sensitive to cost and full market adoption is contingent upon reducing costs below alternatives. Large-scale bulk protein applications for human and animal nutrition are particularly cost sensitive as they compete with cheap soymeal, the largest source of plant-based protein and the primary component in animal feed. Fermentation feedstock, in this instance methanol, comprises most of the cost. As such, effectively reducing the effective cost of methanol is paramount to successful adoption of methylotroph fermentation technology. There are other costs involved in the process and reducing those costs are also critical for adoption.

The embodiments described herein provide a method and associated system to reduce the cost of methylotroph fermentation for SCP applications as well as for low-cost production of biomolecules including, but not limited to, proteins, biopolymers, oils and fatty acids, carbohydrates, etc., and/or simpler molecules produced by methylotrophicic organisms via integration of upstream methanol synthesis with downstream fermentation. Nonlimiting examples of methylotrophic organisms include but are not limited to yeasts, such as *Pichia pastoris*, as well as bacteria such as *Methyophilus methylotrophus, Methylobacterium extorquens, Methylomonas methanolica, Pseudomonas methanolica*, and others. Biomolecules may either be excreted and separated from fermentation media or retained within the whole cell. In the latter situation, the whole cells containing biomolecules are then either separated and dried or alternatively extracted via cell separation, lysing, and biomolecule purification. With respect to protein, applications include the production of heterologous protein/peptide biopharmaceuticals, industrial enzymes, and analytical proteins, as well as bulk protein that may either be extracted or retained within whole cells and used as human and animal nutritional additives. Further, the system and methods described herein integrate upstream methanol synthesis with downstream methylotroph fermentation, and greatly reduce overall cost of biomolecular production by eliminating the need for methanol distillation columns that are both costly and energy consuming.

FIG. 1 is a block diagram illustrating an exemplary integrated system 100 for growing and isolating whole cells in accordance with at least one embodiment of the disclosure. The integrated system 100 includes a methanol synthesis apparatus 102, which includes a syngas unit 104 for generating syngas (a mixture of $H_2$ and carbon monoxide) and a syngas-to-methanol unit 106. In some embodiments, the methanol synthesis apparatus 102 generates unrefined methanol by excluding or bypassing any distillation apparatus or other apparatus that would typically be used to purify the unrefined methanol. In some embodiments, the unrefined methanol includes methanol, a smaller amount of water, higher alcohols, and/or other organic molecules. In some embodiments, the unrefined methanol is directly mixed with water and other nutrients 108 via a media mixing apparatus 110 to produce a growth medium that is then metered via a metering apparatus 112 into a fermentation vessel 114. In some embodiments, the fermentation vessel 114 is used to grow methylotrophic organisms in a fermentation medium 116. In some embodiments, more than one fermentation vessel 114 may be utilized (e.g., for growing multiple batches of organisms or different organisms). In a preferred embodiment, methanol is both the main carbon and energy source (although it is recognized that glycerol, glucose, or other carbon sources may be used in an initial cell expansion growth phase). It is further understood that additional nutrients used for cell growth including but not limited to: biotin, yeast extract, soytone, yeast nitrogen base, potassium phosphate monobasic, potassium phosphate dibasic, $H_3PO_4$, $CaSO_4$, $K_2SO_4$, $MgSO_4$, KOH, $CuSO_4$, IK, $MnSO_4$, $Na_2MoO_4$, $H_3BO_3$, $CoCl_2$, $ZnSO_4$, Fe(II)$SO_4$, and $H_2SO_4$.

In some embodiments, the methanol synthesis apparatus 102 is adapted to produce syngas from a carbon feedstock 118, which may include, but is not limited to, natural gas/methane, coal, biomass, sewage, sludge, municipal waste, or $CO_2$. The methanol synthesis apparatus 102 may be adapted to process the syngas via steam methane reforming (SMR), partial oxidation of methane (POx), dry-reforming, tri-reforming, or other methods known in the art for converting syngas into methanol.

In some embodiments, the fermentation vessel 114 has at least one inlet port and is in communication with the metering apparatus 112 to receive the growth medium. The fermentation vessel 114 may also be in communication with and have associated output ports for a temperature control apparatus, such as a chilling apparatus 120 (e.g., an adsorption chiller). A cell separation apparatus 124 may be used to separate whole cells from the fermentation medium 116 to produce a stream of whole cells and a whole cell-depleted stream 126. In some embodiments, the whole cell-depleted stream 126 is reintroduced into the fermentation vessel 114. In other embodiments, the whole cells may be discarded in the case where biomolecules are to be produced. In some embodiments, the stream of whole cells is sent to a drying apparatus 128 for drying the whole cells 130. The fermentation vessel 114 may also have one or more inlet ports to receive cooled fermentation media from the chilling apparatus 120.

In some embodiments, the fermentation vessel 114 may further be equipped with a mixing apparatus 134, defoaming mechanisms, an array of sensors (sensors for measuring, for example, temperature, turbidity, oxygenation, $CO_2$, MeOH, etc.), or other components as would be appreciated by those of ordinary skill in the art.

Given that methylotrophs are generally aerobic organisms, in some embodiments, the fermentation vessel 114 is in communication with an oxygenation unit 136 that introduces an oxygen-containing gas 138 into the fermentation vessel 114. The oxygen-containing gas 138 may include air, purified oxygen, or other mixtures comprising oxygen and $CO_2$, argon, $N_2$, or other gaseous species (such as volatile organic compounds).

In some embodiments, oxygen from the oxygen-containing gas 138 is dissolved into the fermentation medium 116 in which methylotrophic organisms are growing through a variety of mechanisms including, but not limited to, bubbling, jet aeration, sparging, spraying fermentation medium 116 through the oxygen-containing gas 138, and other methods appreciated by those of ordinary skill in the art. In some embodiments, nanoscale bubbles (e.g., median of less than about 200 nm in diameter) are introduced into the fermentation medium 116. The nanoscale bubbles may be small enough to have a surface charge such that they remain in suspension, and can vastly increase oxygen transfer. In some embodiments, a nanoscale bubble generation apparatus (e.g., produced by Moleaer) is utilized. Purified oxygen may be optionally generated using techniques known in the art including, but not limited to, temperature swing adsorption and pressure swing adsorption systems that utilize adsorbents, such as molecular sieves, zeolites, and other materials. Thermal energy to drive a temperature swing adsorption system may be derived from a waste steam produced by the methanol synthesis apparatus 102.

Methylotrophic organisms produce carbon dioxide as a result of biological respiration, which will separate and rise along with other dissolved gases (including undissolved oxygen or nitrogen if air is used as the oxygen-containing gas 138) into a $CO_2$-containing offgas. In some embodiments, the offgas may be removed from the fermentation vessel 114 via an outlet port. In some embodiments, the offgas may be separated by a gas separation unit 140 into a concentrated $CO_2$ gas stream and a second $CO_2$-depleted gas stream (e.g., which may contain a high concentration of oxygen). The gas separation unit 140 may be, for example, a pressure swing adsorption system or a temperature swing adsorption system that uses molecules (including liquids and polymers) having one or more amine moieties. Additional units for gas separation may utilize size selective molecular sieves and/or zeolites to separate $CO_2$ from other gases. The concentrated $CO_2$ gas stream may be directed to the methanol synthesis apparatus 102 to increase the methanol production output. The $CO_2$-depleted gas stream, which may have a high concentration of oxygen, may be recycled by directing it to the oxygenation unit 136 for introduction into the fermentation vessel 114 (which may be optionally mixed with oxygen-containing gas 138).

Methylotrophic organisms dispersed within an aqueous fermentation medium 116 may or may not excrete protein or other biomolecules into the fermentation medium 116. All or a portion of the fermentation medium 116 with whole cells may be extracted from the fermentation vessel 114 into an output stream. In some embodiments, the output stream may be separated via the cell separation apparatus 124 into a concentrated whole cell stream and a whole cell-depleted stream 126. The whole cell-depleted stream 126 may be recycled back into the fermentation vessel 114. In some embodiments, the concentrated whole cell stream may be subjected to lysis followed by purification to isolate the desired biomolecules which may introduced into the drying apparatus 128. In some embodiments, the concentrated whole cell stream (with protein, oils, and/or other biomolecules contained within the whole cells) is introduced into the drying apparatus 128 to produce dried whole cells 130. Exemplary and non-limiting examples of the cell separation apparatus 124 include centrifuges, continuous flow centrifuges, and filters, such as microfilters and ultrafilters having an average pore size smaller than the average diameters of the whole cells.

Figure 2:
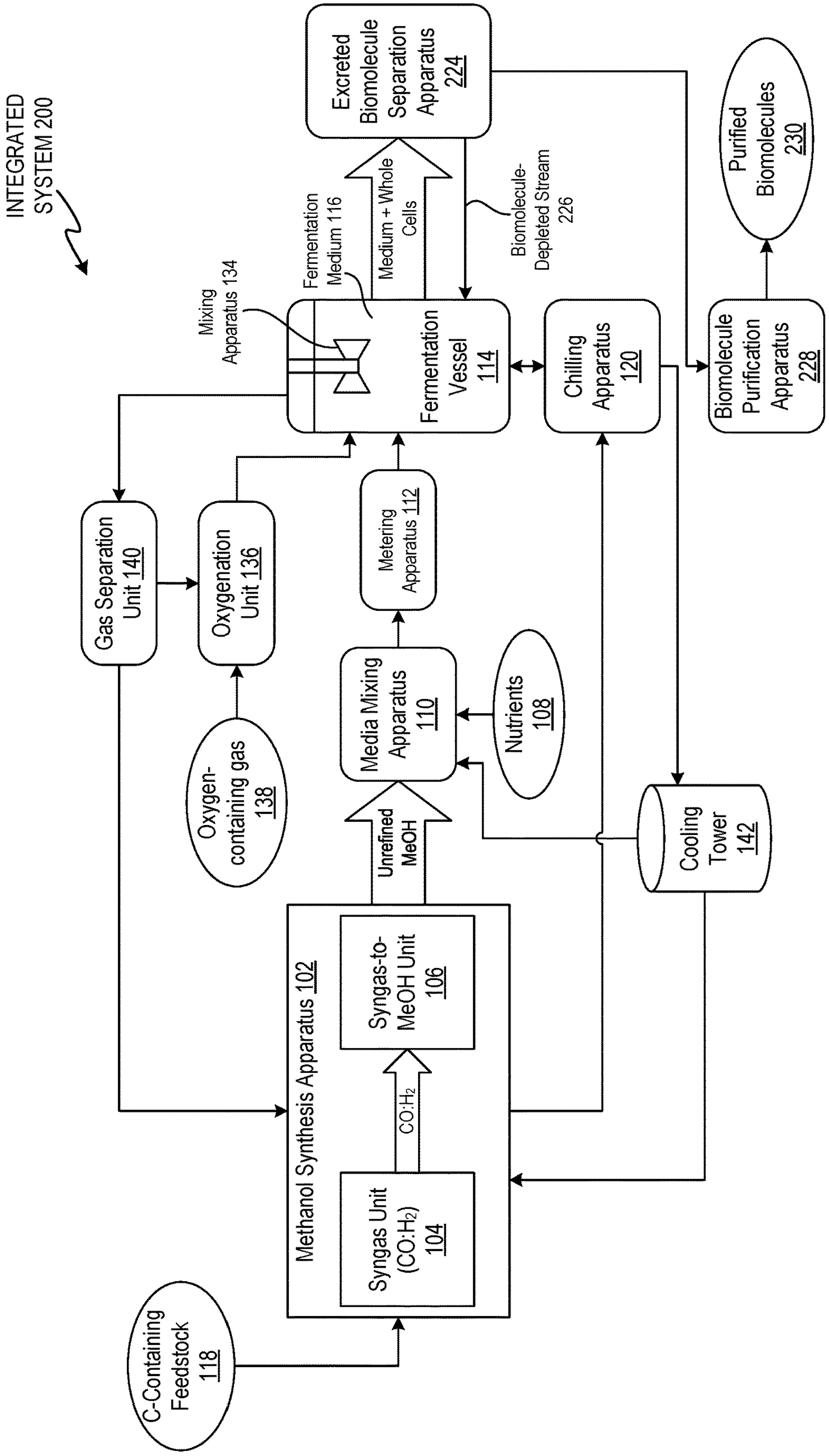
FIG. 2 is a block diagram illustrating an exemplary integrated system for separating excreted biomolecules in accordance with at least one embodiment of the disclosure.

In a variant of the integrated system 100, FIG. 2 is a block diagram illustrating an exemplary integrated system 200 for separating excreted biomolecules in accordance with at least one embodiment of the disclosure. The integrated system 200 includes an excreted biomolecule separation apparatus 224 that receives an output stream from the fermentation vessel including the fermentation medium 116, whole cells, and biomolecules excreted from the whole cells. The excreted biomolecule separation apparatus 224 may be a centrifuge, a cross flow filter, or other device capable of separating out higher molecular weight protein from the liquid fraction and smaller molecular weight fractions. In some embodiments, the excreted biomolecule separation apparatus 224 may separate the output stream into a biomolecule-containing stream (which may be provided to a biomolecule purification apparatus 228) and a biomolecule-depleted stream 226 (containing fermentation medium and whole cells) that is reintroduced into the fermentation vessel 114. In some embodiments, biomolecule purification apparatus 228 may use one or more of the following techniques to obtain purified biomolecules 230 including, but not limited to, ultrafiltration, nanofiltration, cross flow filtration, reverse osmosis, ultracentrifugation, precipitation, chromatography, and high pressure liquid chromatography.

Referring to both FIGS. 1 and 2, a high temperature waste steam produced by the methanol synthesis apparatus 102 may be optionally used to provide the heat energy to drive the chilling apparatus 120, which is used to control the temperature of the whole cell/fermentation medium mixture within the fermentation vessel 114 in an optimal temperate range needed for cellular growth (e.g., under 120° F.). In the integrated system 100, in some embodiments, the high temperature steam produced by the methanol synthesis apparatus 102 may be optionally used to drive the drying apparatus 128 to dry extracted and purified whole cells or excreted biomolecules that are produced by methylotrophic organisms in the fermentation vessel 114 and separated by methods described above. In some embodiments, the drying apparatus 128 may be effectuated directly via a superheated steam drying system, or indirectly by using the steam heat to drive heated air dryers. In some embodiments, the heated air dryers may additionally incorporate a spray drying apparatus such that hydrated whole cells or excreted biomolecules are sprayed into droplets exposed to elevated temperature from superheated steam or dry air. Other non-limiting exemplary drying processes include freeze drying and lyophilization.

In some embodiments, steam passing into and through either the drying apparatus 128 or the chilling apparatus 120 may exit as an output stream of lower temperature steam and/or condensed water. The output stream from the drying apparatus 128 and/or the chilling apparatus 120 may be provide to a cooling tower 142 and then optionally recycled back as condensates into the methanol synthesis apparatus 102 and/or the media mixing apparatus 110.

In some embodiments, the high temperature waste steam produced by the methanol synthesis apparatus 102 may be optionally used to provide heat energy for driving a temperature swing adsorption system for the production of the oxygen-containing gas 138 (e.g., purified oxygen), and/or to drive a temperature swing adsorption system used in the gas separation unit 140 to separate offgas $CO_2$ from $O_2$.

The following variations for the integrated system 100 and/or the integrated system 200 are contemplated. In a first embodiment, unrefined methanol may be introduced directly into the fermentation vessel 114 without first being mixed with nutrients 108 by the media mixing apparatus 110. The nutrients 108 may also be introduced directly into the fermentation vessel 114.

In a second embodiment, the chilling apparatus 120 may include a series of tubes that extend into the fermentation vessel 114 and carry a refrigerant that is in fluid communication with the chilling apparatus 120. In some embodiments, the chilling apparatus 120 may include one or more heat pipes that extend into the fermentation vessel 114 in order to remove heat from the fermentation medium 116. In some embodiments, the heat pipes may be configured to rotate around a longitudinal axis of the fermentation vessel, and may include one or more mixing impellers including, but not limited to, Rushton impellers, paddle mixers, and helical mixers.

In a third embodiment, $CO_2$ introduced into the methanol synthesis apparatus 102 may, in addition to or instead of being derived from offgas, be derived from a $CO_2$-rich gas stream including a combustion source, such as a power plant, refinery, cement production facility, etc., or from a direct air $CO_2$ capture apparatus.

In a fourth embodiment, a concentrated $CO_2$ gas stream derived from the offgas separated by the gas separation unit 140 may be electrocatalytically reduced to CO and $O_2$. The CO and $O_2$ may be separated into a CO-rich stream and an $O_2$-rich stream. The CO-rich stream may be introduced into either the syngas unit 104 or the syngas-to-methanol unit 106. The $O_2$-rich stream may be introduced into the oxygenation unit 136.

In a fifth embodiment, the methanol synthesis apparatus 102 may be adapted to produce $H_2$ via electrolysis of water, mix the $H_2$ with $CO_2$ to form a gas mixture, and convert the gas mixture into unrefined methanol.

In a sixth embodiment, nitrogen-containing soluble molecules added to unrefined methanol to form the growth media may be derived from a portion of the $H_2$, derived either through reformation or electrolysis, and catalytically reacted the $H_2$ with $N_2$ to form ammonia via the Haber-Bosch process or other processes that would be appreciated by those of ordinary skill in the art. The ammonia may then be dissolved in water or converted into another nitrogen-containing water soluble molecule including, but not limited to, urea, nitrate salts, amides, etc.

In a seventh embodiment, an elevated $CO_2$ concentration within the fermentation vessel 114 may be effected to improve the efficiency of the gas separation unit 140 particularly when the oxygen-containing gas 138 is purified oxygen. A portion of the offgas stream may be directly introduced into the oxygenation unit 136 without first being subjected to the gas separation unit 140.

It is to be understood that the integrated system 100 and the integrated system 200 are not drawn to scale and may designed to be of any suitable dimensions, and may be modified as desired as would be appreciated by those of ordinary skill in the art. Moreover, some or all of the functionality of each system may be automated.

FIG. 3 is a flow diagram illustrating a method 300 of producing biomolecules or whole cells in accordance with at least one embodiment of the disclosure. The method 300 may be performed, in some embodiments, using the integrated system 100 or integrated system 200.

At block 310, a growth medium comprising unrefined methanol is provided (e.g., by the methanol synthesis apparatus 102). In some embodiments, the unrefined methanol is derived directly from a methanol synthesis apparatus without being subjected to a distillation process. In some embodiments, the unrefined methanol is derived from the methanol synthesis apparatus using a subset of distillation process steps (e.g., light end hydrocarbon removal, such as removal of acetone, dimethyl ether, methyl format, etc., and/or separation of methanol from water and higher alcohols) so as to remove a subset of contaminants present in the unrefined methanol. In some embodiments, the unrefined methanol comprises greater than about 0.5% water and/or less than about 0.1% alcohol having more than 1 carbon atom. In some embodiments, the unrefined methanol is mixed (e.g., via the media mixing apparatus 110) with water and/or various nutrients (e.g., nutrients 108) to produce the growth medium.

At block 320, the growth medium is metered (e.g., via the metering apparatus 112) into a fermentation vessel (e.g., the fermentation vessel 114) comprising an aqueous fermentation medium (e.g., the fermentation medium 116). In some embodiments, the aqueous fermentation medium is selected to promote the maintenance and growth of methylotrophic organisms including one or more of *Pichia pastoris, Methylophilus methylotrophus, Methylobacterium extorquens, Methylomonas methanolica*, or *Pseudomonas methanolica*. In some embodiments, the methylotrophic organisms may be such organisms that utilize a ribose monophosphate pathway, a serine pathway, an alcohol oxidase 1 pathway, and/or an alcohol oxidase 2 pathway.

At block 330, an oxygen-containing gas (e.g., the oxygen-containing gas 138) is introduced into the aqueous fermentation medium within the fermentation vessel. In some embodiments, the oxygen-containing gas comprises air, a mixture of oxygen and at least one other gas, or purified oxygen. In some embodiments, the oxygen-containing gas is introduced in an amount and/or for a time sufficient to expand a population of methylotrophic organisms within the aqueous fermentation medium, where the amount and duration of the gas introduction, as well as the conditions of the fermentation medium, are readily ascertainable by one of ordinary skill in the art. In some embodiments, the oxygen-containing gas is introduced into the aqueous fermentation medium via jet aeration, surface aeration, or fine bubble diffusers. In some embodiments, the oxygen-containing gas is introduced into the fermentation medium in a form of bubbles having a median diameter of less than about 200 nm.

In some embodiments, a carbon dioxide-containing waste gas mixture is evolved from the whole cells in the fermentation vessel, and carbon dioxide is separated from other gases within the waste gas mixture (e.g., via the gas separation unit 140) into a concentrated carbon dioxide gas stream and a carbon dioxide-depleted gas stream. In some embodiments, the carbon dioxide is separated from the other gases via exposure to molecules comprising one or more amine moieties or exposure to size selective molecular sieves or zeolites. In some embodiments, the concentrated carbon dioxide gas stream is introduced into the methanol synthesis apparatus. In some embodiments, the carbon dioxide-depleted gas stream is introduced into the fermentation vessel (e.g., after oxygenation with an oxygen-containing gas 138 via the oxygenation unit 136).

In some embodiments, a chilling apparatus (e.g., the chilling apparatus 120) is used to maintain a temperature of the aqueous fermentation medium at below 120° F. In some embodiments, the chilling apparatus comprises an adsorption chiller. In some embodiments, thermal energy used by adsorption chiller is derived from steam generated by the methanol synthesis apparatus.

At block 340, whole cells (e.g., of the methylotrophic organisms) or biomolecules excreted by the whole cells into the aqueous fermentation medium are separated from the aqueous fermentation medium (e.g., via the cell separation apparatus 124 for whole cell separation, or via the excreted biomolecule separation apparatus 224 for excreted biomolecules). In some embodiments, the whole cells are separated by extracting a portion of the aqueous fermentation medium comprising the whole cells, concentrating the whole cells into a first stream and whole cell-depleted fermentation medium into a second stream, and optionally reintroducing the second stream into the fermentation vessel. In some embodiments, a portion of the aqueous fermentation medium is passed through a filter comprising pores, where the pores have an average diameter of less than an average diameter of the whole cells. In some embodiments, the filter comprises a nanofiltration membrane, an ultrafiltration membrane, or a microporous filter.

In some embodiments, the whole cells are concentrated into the first stream by exposing the aqueous fermentation medium to centrifugal force. In some embodiments, the whole cells are concentrated via centrifugation or continuous flow centrifugation. In some embodiments, the concentrated whole cells are dried via exposure to superheated steam or lysed via exposure to the superheated steam. In some embodiments, the superheated steam is derived from the methanol synthesis apparatus. In some embodiments, steam or superheated steam is reintroduced back into the methanol synthesis apparatus after drying the concentrated whole cells.

In some embodiments, the whole cells are dried via exposure to hot gas (e.g., air, nitrogen, argon, helium, or carbon dioxide). In some embodiments, the hot gas is derived from steam from the methanol synthesis apparatus. In some embodiments, the whole cells are dried via spray drying, microwave drying, freeze drying, or lyophilization.

In the foregoing description, numerous specific details are set forth, such as specific materials, dimensions, processes parameters, etc., to provide a thorough understanding of the embodiments of the present disclosure. The particular features, structures, materials, or characteristics may be combined in any suitable manner in one or more embodiments. The words "example" or "exemplary" are used herein to mean serving as an example, instance, or illustration. Any aspect or design described herein as an "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or." That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the use of the terms "a," "an," "the," and similar referents in the context of describing the materials and methods discussed herein (especially in the context of the following claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Reference throughout this specification to "one embodiment," "certain embodiments," "one or more embodiments," "an embodiment," or "some embodiments" means that a particular feature, structure, material, or characteristic described in connection with the embodiment is included in at least one embodiment of the present disclosure. Thus, the appearances of the phrases such as "in one or more embodiments," "in certain embodiments," "in one embodiment," or "in an embodiment" in various places throughout this specification are not necessarily referring to the same embodiment of the present disclosure. Furthermore, the particular features, structures, materials, or characteristics may be combined in any suitable manner in one or more embodiments.

It is to be understood that the above description is intended to be illustrative, and not restrictive. Many other embodiments will be apparent to those of skill in the art upon reading and understanding the above description. The scope of the disclosure should, therefore, be determined with reference to the appended claims, along with the full scope of equivalents to which such claims are entitled. The use of any and all examples, or exemplary language (e.g., "such as") provided herein, is intended merely to illuminate certain materials and methods and does not pose a limitation on scope. No language in the specification should be construed as indicating any non-claimed element as essential to the practice of the disclosed materials and methods.

Although the embodiments disclosed herein have been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents, and the above-described embodiments are presented for the purposes of illustration and not of limitation.

What is claimed is:

1. A method of producing whole cells, the method comprising:

providing, by a media mixing apparatus, a growth medium comprising unrefined methanol generated by a methanol synthesis apparatus;

metering the growth medium into a fermentation vessel comprising an aqueous fermentation medium;

introducing an oxygen-containing gas into the aqueous fermentation medium within the fermentation vessel and expanding a population of methylotrophic organisms within the aqueous fermentation medium;

extracting a portion of the aqueous fermentation medium comprising the whole cells;

concentrating the whole cells into a first stream and whole cell-depleted fermentation medium into a second stream;

introducing the first stream into a drying apparatus to dry the whole cells;

recycling an output stream from the drying apparatus to the methanol synthesis apparatus and the media mixing apparatus, wherein the output stream from the drying apparatus comprises low temperature steam; and directing the output stream to a cooling tower to condense the low temperature steam to an aqueous liquid prior to recycling the output stream from the drying apparatus to the methanol synthesis apparatus and/or the media mixing apparatus.

2. The method of claim 1, wherein the unrefined methanol is derived from the methanol synthesis apparatus without being subjected to a distillation process, or by being subjected to a subset of steps of the distillation process.

3. The method of claim 1, wherein the oxygen-containing gas is introduced into the aqueous fermentation medium via jet aeration, surface aeration, or fine bubble diffusers, and wherein the oxygen-containing gas comprises air, a mixture of oxygen and at least one other gas, or purified oxygen.

4. The method of claim 3, wherein the oxygen-containing gas is introduced into the aqueous fermentation medium in a form of bubbles having a median diameter of less than about 200 nm.

5. The method of claim 1, wherein the methylotrophic organisms comprise one or more of *Pichia pastoris, Methylophilus methylotrophus, Methylobacterium extorquens, Methylomonas methanolica*, or *Pseudomonas methanolica.*

6. The method of claim 1, wherein the methylotrophic organisms utilize a ribose monophosphate pathway, a serine pathway, an alcohol oxidase 1 pathway, and/or an alcohol oxidase 2 pathway.

7. The method of claim 1, further comprising:

reintroducing at least a portion of the second stream into the fermentation vessel.

8. The method of claim 7, further comprising:

passing the portion of the aqueous fermentation medium through a filter comprising pores, wherein the pores have an average diameter of less than average diameters of the whole cells.

9. The method of claim 7, wherein concentrating the whole cells into the first stream comprises exposing the aqueous fermentation medium to centrifugal force.

10. The method of claim 7, further comprising:

drying the concentrated whole cells by the drying apparatus via exposure to superheated steam.

11. The method of claim 10, wherein the superheated steam is derived from the methanol synthesis apparatus.

12. The method of claim 7, further comprising:

drying the concentrated whole cells by the drying apparatus via exposure to hot gas; or lysing the whole cells via exposure to the hot gas.

13. The method of claim 12, wherein the hot gas is generated from steam from the methanol synthesis apparatus.

14. The method of claim 7, further comprising:

drying the concentrated whole cells via spray drying, microwave drying, freeze drying, or lyophilization.

15. The method of claim 1, further comprising:

extracting a carbon dioxide-containing waste gas mixture evolved from the whole cells in the fermentation vessel; and separating carbon dioxide from other gases within the waste gas mixture into a concentrated carbon dioxide gas stream and a carbon dioxide-depleted gas stream.

16. The method of claim 15, wherein the carbon dioxide is separated from the other gases via exposure to molecules comprising one or more amine moieties or exposure to size selective molecular sieves or zeolites.

* * * * *